(12) United States Patent
Agnew

(10) Patent No.: US 8,317,853 B2
(45) Date of Patent: Nov. 27, 2012

(54) PROSTHETIC VALVE WITH EXTERNAL SUPPORT FRAME

(75) Inventor: Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 49 days.

(21) Appl. No.: 13/118,724

(22) Filed: May 31, 2011

(65) Prior Publication Data

US 2011/0288621 A1   Nov. 24, 2011

Related U.S. Application Data

(63) Continuation of application No. 11/061,352, filed on Feb. 18, 2005, now Pat. No. 7,955,375.

(60) Provisional application No. 60/546,532, filed on Feb. 20, 2004.

(51) Int. Cl.
*A61F 2/24* (2006.01)

(52) U.S. Cl. .................. 623/1.24; 623/1.26; 623/2.17

(58) Field of Classification Search ........ 623/1.24–1.26, 623/2.1–2.19; *A61F 2/24*
See application file for complete search history.

(56) References Cited

U.S. PATENT DOCUMENTS

| | | |
|---|---|---|
| 4,222,126 A | 9/1980 | Boretos et al. |
| 4,580,568 A | 4/1986 | Gianturco |
| 5,314,473 A | 5/1994 | Godin |
| 6,206,931 B1 | 3/2001 | Cook et al. |
| 6,231,598 B1 | 5/2001 | Berry et al. |
| 6,299,604 B1 | 10/2001 | Ragheb et al. |
| 6,299,635 B1 | 10/2001 | Frantzen |
| 6,358,284 B1 | 3/2002 | Fearnot et al. |
| 6,458,153 B1 | 10/2002 | Bailey et al. |
| 6,464,720 B2 | 10/2002 | Boatman et al. |
| 6,494,909 B2 | 12/2002 | Greenhalgh |
| 6,508,833 B2 | 1/2003 | Pavcnik et al. |
| 6,666,892 B2 | 12/2003 | Hiles et al. |
| 2001/0039450 A1 | 11/2001 | Pavcnik et al. |
| 2001/0041928 A1 | 11/2001 | Pavcnik et al. |
| 2004/0044407 A1 | 3/2004 | Verona et al. |
| 2004/0106976 A1 | 6/2004 | Bailey et al. |
| 2004/0117004 A1 | 6/2004 | Osborne et al. |
| 2004/0225352 A1 | 11/2004 | Osborne et al. |

FOREIGN PATENT DOCUMENTS

| | | |
|---|---|---|
| WO | WO0156500 | 8/2001 |
| WO | WO02024119 | 3/2002 |
| WO | WO2004080352 | 9/2004 |

*Primary Examiner* — Chistopher D Koharski
*Assistant Examiner* — Jason-Dennis Stewart
(74) *Attorney, Agent, or Firm* — Buchanan Nipper

(57) ABSTRACT

Prosthetic valves, methods of making medical devices, and methods of treatment are provided. The prosthetic valves of the invention have a valve portion moveable between first and second positions, and a spacing member that has a thickness and protects a portion of the valve portion from contact with a wall of a vessel in which the prosthetic valve is implanted, and/or another structural component of the prosthetic valve, such as a support frame.

20 Claims, 9 Drawing Sheets

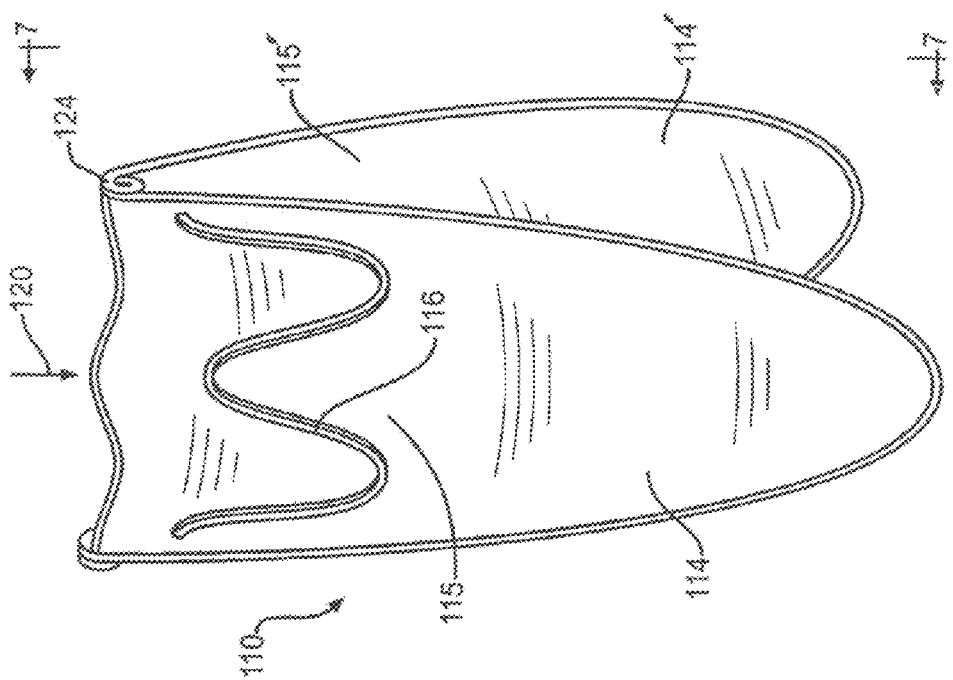
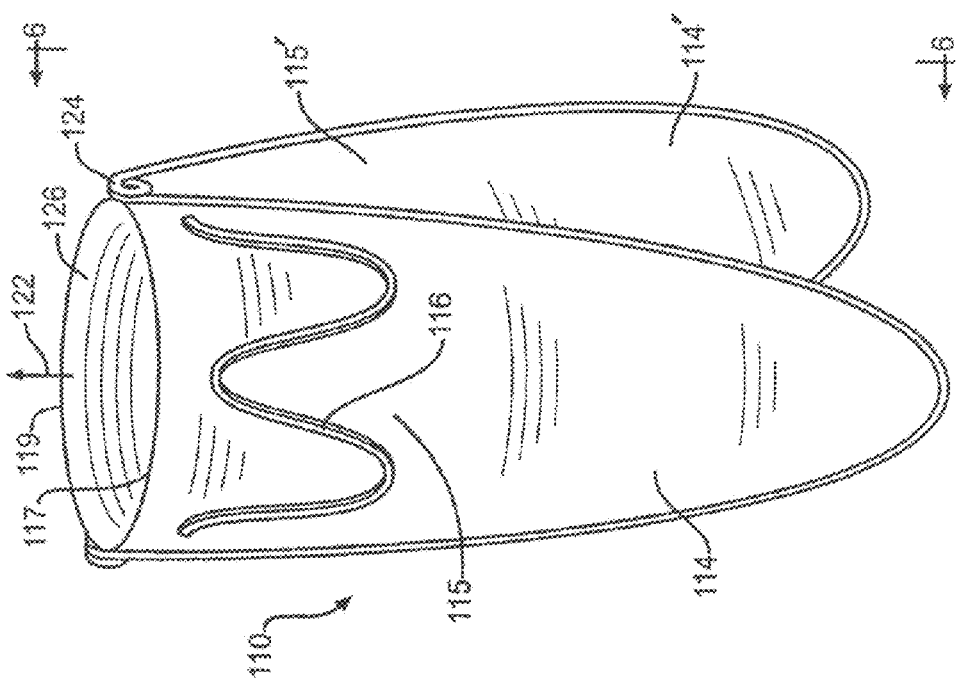

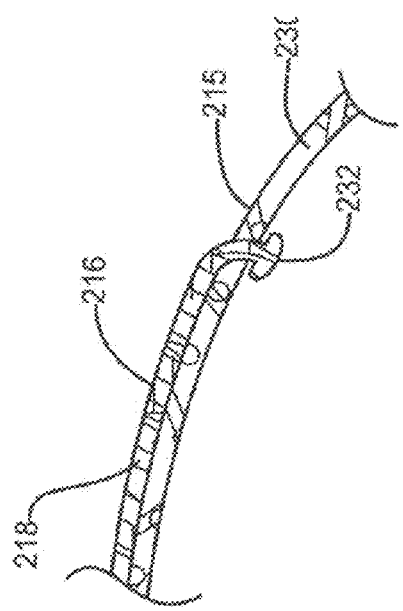
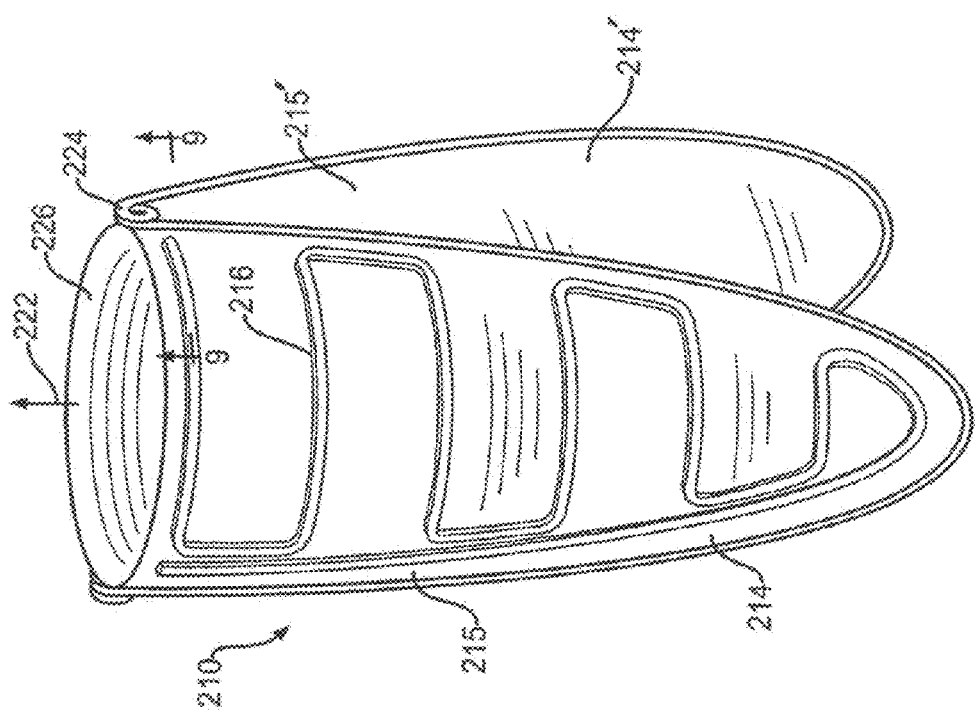

PROSTHETIC VALVE WITH EXTERNAL SUPPORT FRAME

CROSS-REFERENCE TO RELATED APPLICATIONS

This application is a continuation of U.S. Non-Provisional application Ser. No. 11/061,352, which was filed on Feb. 18, 2005 and which claims priority to U.S. Provisional Application No. 60/546,532 filed on Feb. 20, 2004. The disclosure of each of these related applications is hereby incorporated into this disclosure in its entirety.

FIELD OF THE INVENTION

The present invention relates to medical devices. More particularly, the invention relates to prosthetic valves for implantation in a body vessel.

BACKGROUND OF THE INVENTION

Many vessels in animals transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction and close to prevent fluid flow in a reverse direction, i.e., retrograde flow. The valves can change from an open position to a closed position in response to a variety of circumstances, including changes in the cross-sectional shape of the vessel and the fluid pressure within the vessel.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, and can lead to discomfort and possibly ulcers in the legs and ankles.

Current treatments for venous valve insufficiency include the use of compression stockings that are placed around the leg of a patient in an effort to force the vessel walls radially inward to restore valve function. Surgical techniques are also employed in which valves can be bypassed, eliminated, or replaced with autologous sections of veins with competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like.

Recently, prosthetic valves that are implantable by minimally invasive techniques have been developed. Frequently, a graft member is attached to a support frame and provides a valve function to the device. For example, the graft member can be in the form of a leaflet that is attached to a support frame and movable between first and second positions. In a first position, the valve is open and allows fluid flow to proceed through a vessel in a first direction, and in a second position the valve is closed to prevent fluid flow in a second, opposite direction. Examples of this type of prosthetic valve are described in commonly owned U.S. Pat. No. 6,508,833 to Pavcnik for a MULTIPLE-SIDED INTRALUMINAL MEDICAL DEVICE, United States Patent Application Publication No. 2001/0039450 to Pavcnik for an IMPLANTABLE VASCULAR DEVICE, and U.S. patent application Ser. No. 10/642,372, filed on Aug. 15, 2003, all of which are hereby incorporated by reference in their entirety. In other examples of prosthetic valves, a tube that terminates in leaflets is attached to one or more support frames to form a valve. The leaflets open to permit fluid flow in a first direction in response to fluid pressure on one side of the leaflets, and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

Some materials used in prosthetic valves may be capable of adhering to or becoming incorporated into the wall of a vessel in which the valve is implanted. For example, some graft materials may adhere to a vessel wall if thrombus forms on or near the material. Also, some natural materials, such as bioremodellable materials, may become incorporated into the vessel wall due to cellular in-growth, bioremodelling, or other processes.

Adherence and/or incorporation of a portion of a prosthetic valve may be desirable in some circumstances. For example, adherence of a portion of a graft material of a prosthetic valve to a vessel wall may facilitate anchoring of the valve within the vessel. However, it may be desirable to prevent adherence and/or incorporation in some circumstances. For example, if a portion of a prosthetic valve requires movement to retain function, such as a valve leaflet or a portion of a leaflet, adherence and/or incorporation of that portion may affect performance of the prosthetic valve. Furthermore, mechanical interaction between a movable portion, such as a valve leaflet or portion of a leaflet, and another structural component, such as a portion of a support frame, may also be undesirable.

SUMMARY OF THE EXEMPLARY EMBODIMENTS OF THE INVENTION

The invention provides prosthetic valves that include one or more elements that protect a moveable portion of the valve from adherence and/or incorporation into a tissue, such as a vessel wall, and/or from mechanical interaction with another structural component of the valve, such as a portion of a support frame.

The invention provides prosthetic valves for implantation in a body vessel. In one embodiment, a prosthetic valve according to the invention comprises a valve member comprising a valve portion movable between first and second positions. A spacing member is disposed on the valve portion and has a pre-determined thickness. The spacing member protects the valve portion from contact with the wall of the body vessel in which the prosthetic vessel is implanted.

In another embodiment, a prosthetic valve according to the invention comprises an expandable support frame and a valve member attached to the support frame. The valve member comprises a valve portion movable between first and second positions. A spacing member is disposed on the support frame and has a predetermined thickness.

In another embodiment, a prosthetic valve according to the invention comprises an expandable support frame and a valve member attached to the support frame. The valve member comprises a valve portion moveable between first and second positions. A spacing member is disposed on the support frame and has a predetermined thickness.

In another embodiment, a prosthetic valve according to the invention comprises a first movable leaflet having a first edge and a second movable leaflet having a second edge. The first and second edges cooperate to define a temporary opening. A first spacing member is disposed on the first movable leaflet and a second spacing member is disposed on the second movable leaflet.

In another embodiment, a prosthetic valve according to the invention comprises an expandable support frame and a valve member attached to the support frame. The valve member comprises a valve portion that is movable between first and second positions. The prosthetic valve further comprises a pouch that defines a cavity. A portion of the support frame and a portion of the valve member are disposed in the cavity of the pouch.

In another embodiment, a prosthetic valve according to the invention comprises a valve member comprising a valve portion movable between first and second positions, and a resorbable support frame disposed on the valve portion.

The invention also provides methods of making prosthetic valves for implantation in a body vessel. One method according to the invention comprises providing a valve member comprising a valve portion movable between first and second positions, and disposing a spacing member on the valve portion.

Another method of making a prosthetic valve according to the invention comprises providing a valve member comprising a valve portion movable between first and second positions and having a thickness, providing a spacing member, disposing a portion of the spacing member on the valve portion, and passing a portion of the spacing member through the thickness of the valve member.

Another method of making a prosthetic valve according to the invention comprises providing a valve member comprising a valve portion movable between first and second positions and having a thickness, providing a spacing member, and repeatedly passing the spacing member through the thickness of the valve member.

Another method of making a prosthetic valve according to the invention comprises providing a valve member comprising a valve portion movable between first and second positions, providing a pouch defining a cavity, and disposing a portion of the valve member in the cavity.

Another method of making a prosthetic valve according to the invention comprises providing a resorbable valve frame, providing a valve member, and attaching the valve member to the support frame so that the valve member comprises a valve portion moveable between first and second positions and the support frame temporarily maintains the valve portion in the first position.

The invention also provides methods of treatment. One method of treatment according to the invention comprises providing a prosthetic valve comprising a valve member that comprises a valve portion movable between first and second positions, and a support frame attached to the valve portion and adapted to maintain the valve portion in the first position for a period of time. Another step comprises implanting the prosthetic valve in a body vessel.

The invention includes other embodiments within the scope of the claims, and variations on all embodiments. Additional understanding of the invention can be obtained by reviewing the detailed description of exemplary embodiments of the invention, below, and the appended drawings.

BRIEF DESCRIPTION OF THE DRAWINGS

FIG. 4 is a perspective view of a prosthetic valve according to one embodiment of the invention.

FIG. 5 is a perspective view of the valve illustrated in FIG. 4, shown in a closed configuration.

FIG. 8 is a perspective view of a prosthetic valve according to one embodiment of the invention.

FIG. 9 is a side view of a portion of the valve illustrated in FIG. 8.

DETAILED DESCRIPTION OF EXEMPLARY EMBODIMENTS OF THE INVENTION

The following detailed description and appended drawings describe and illustrate various exemplary embodiments of the invention. The description and drawings serve to enable one skilled in the art to make and use the invention, and are not intended to limit the scope of the invention in any manner.

The invention provides medical devices for implantation in a body vessel, methods of making the medical devices, and methods of treatment that utilize the medical devices.

Figure 1:
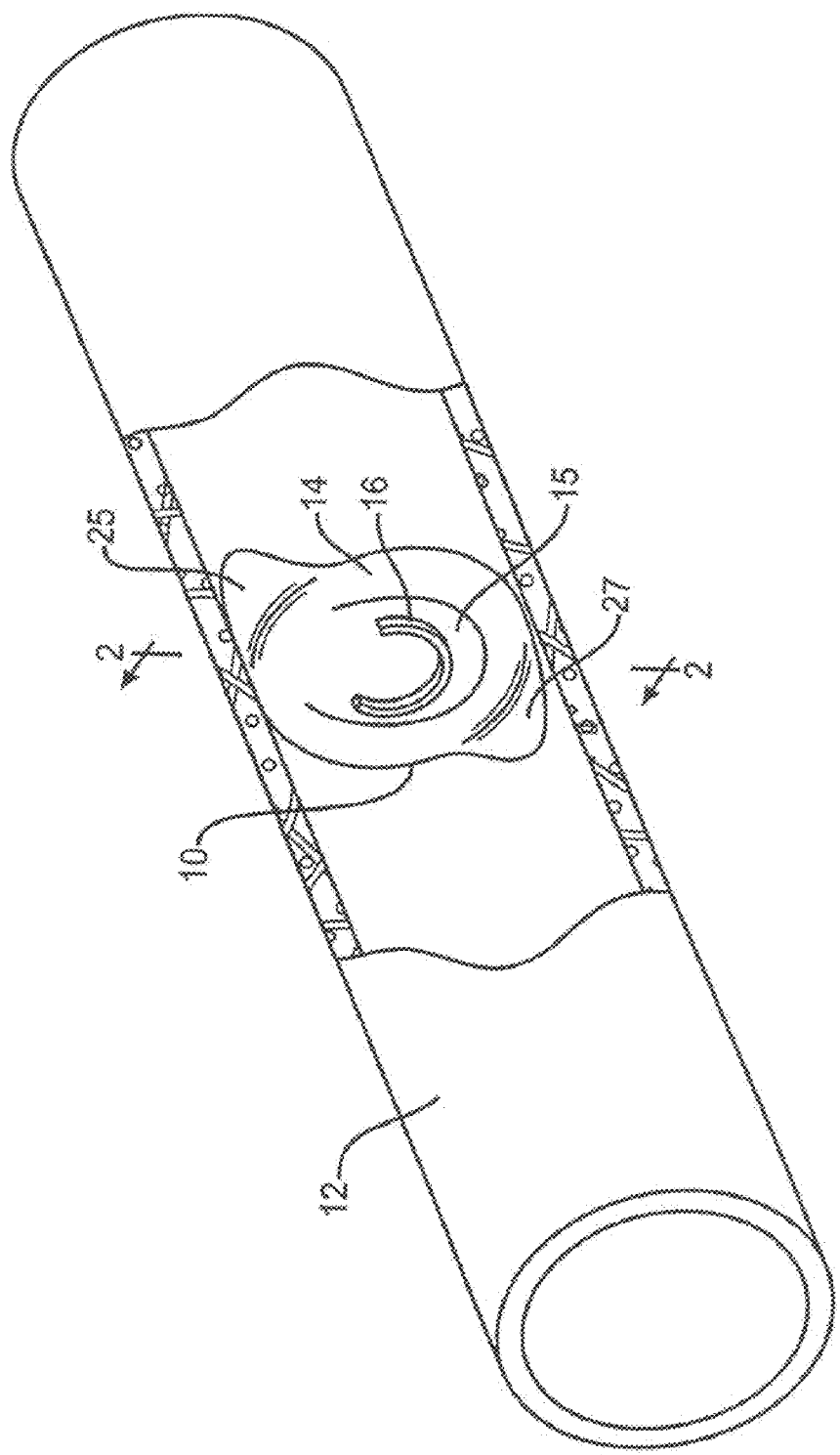
FIG. 1 is a perspective view of a prosthetic valve according to one embodiment of the invention in a body vessel.
Figure 3:
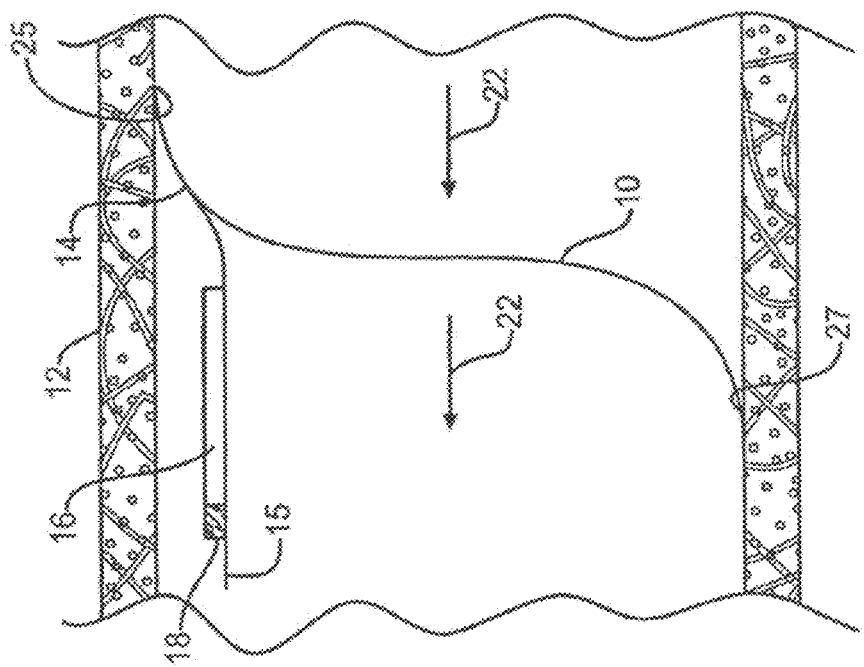
FIG. 3 is a sectional view of the vessel and valve illustrated in FIG. 1 showing the valve in an open configuration.
Figure 2:
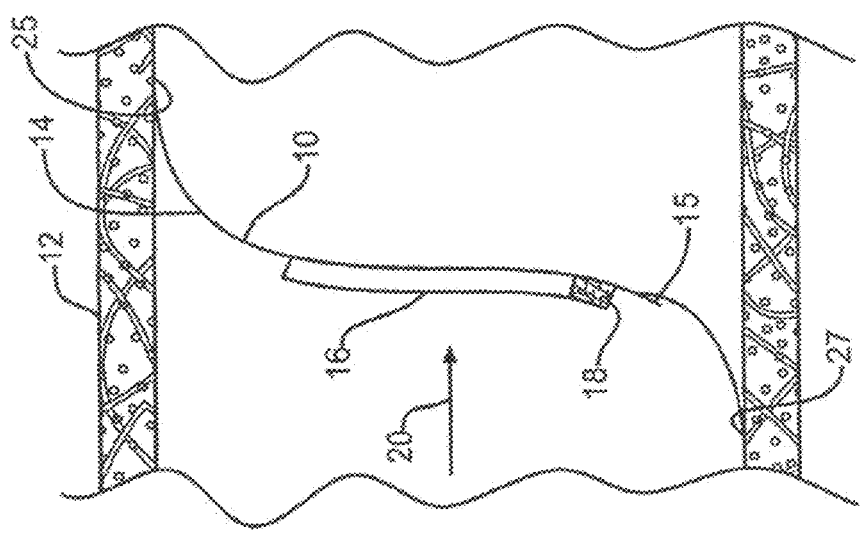
FIG. 2 is a sectional view of the vessel and valve illustrated in FIG. 1, taken along line 2-2.

FIGS. 1 through 3 illustrate a medical device according to a first embodiment of the invention. The device comprises a prosthetic valve 10 that is shown implanted in a body vessel 12. As used herein, the term "implanted" refers to the positioning of a medical device at a location within a body, such as within a body vessel. Furthermore, the term "implantable" refers to an ability of a medical device to be positioned at a location within a body, such as within a body vessel.

The prosthetic valve 10 comprises a valve member 14 that comprises a valve portion 15. The valve member 14 is positioned within a lumen of a body vessel and regulates the flow of fluid through the lumen. The valve portion 15 is a portion of the valve member 14 and is movable between first and second positions. Movement of the valve member 15 between these positions effects the opening and closing of an opening of the prosthetic valve 10, which controls the flow of fluid through the lumen of the vessel.

A spacing member 16 is disposed on the valve portion 15 and has a predetermined thickness 18. As illustrated in FIG. 1, the valve member 14 can comprise a section of material, such as an extracellular matrix (ECM) material, implanted in the vessel. The valve portion 15 can comprise any suitable moveable section of the member 14, such as a flap formed by a slit or other discontinuity in a surface of the valve member 14.

FIGS. 2 and 3 illustrate movement of the valve portion 15 between the first and second positions. In the body vessel 12, fluid flow in one direction, represented by arrow 20, results in fluid pressure on one side of the prosthetic valve 10 and forces the valve portion 15 into the first position. As illustrated in FIG. 3, fluid flow in an opposite direction, represented by arrow 22, produces fluid pressure on an opposing side of the valve portion 15 and forces the valve portion 15 into the second position. As a prosthetic valve, the valve portion 15 can be considered in a closed configuration in response to fluid flow 20. In this configuration, the prosthetic valve 10 substantially prevents fluid from passing through the valve 10. In response to fluid flow in the opposite direction 22, the valve portion 15 can be considered in an open configuration, in which the prosthetic valve 10 allows fluid flow 22 to pass through the valve 10.

The valve member 14 can comprise any suitable material for implantation in a body vessel. The valve member 14 need only be able to provide the moveable valve portion 15, and should be biocompatible or be able to be made biocompatible. Examples of suitable materials for the valve member include natural materials, synthetic materials, and combinations thereof. Examples of suitable natural materials include ECMs, such as small intestine submucosa (SIS), and other bioremodellable materials, such as bovine pericardium. Other examples of ECM materials that can be used in the prosthetic valves of the invention include stomach submucosa, liver basement membrane, urinary bladder submucosa, tissue mucosa, and dura mater. Examples of suitable synthetic materials include polymeric materials, such as expanded polytetrafluoroethylene and polyurethane. ECMs are particularly well suited materials for use in the valve member 14, at least because of their abilities to remodel and become incorporated into adjacent tissues. These materials can provide a scaffold onto which cellular ingrowth can occur, eventually allowing the material to remodel into a structure of host cells. The ability of an ECM to become incorporated into the vessel wall could allow for a prosthetic valve that does not include a support frame, such as a stent. FIGS. 1 through 3 illustrate such a prosthetic valve.

SIS is particularly well suited for use as the valve member 14 for several reasons. For example, SIS is a well-characterized ECM, is able to remodel, and is durable in the presence of blood flow. Methods for preparing SIS are disclosed in a number of U.S. Patents, including U.S. Pat. Nos. 6,206,931, 6,358,284, and 6,666,892, each of which is hereby incorporated by reference in its entirety. SIS is commercially available from Cook Biotech, Inc. of West Lafayette, Ind.

The spacing member 16 has a thickness 18 and is disposed on the valve portion 15 of the valve member 14. As used herein, the term "disposed on" refers to a spatial relationship between the spacing member 16 and the valve portion 15, and requires only that the spacing member 16 be adjacent the valve portion 15. The term does not require direct contact between the spacing member 16 and valve portion 15, nor does it require attachment between these elements, although both of these spatial relationships are encompassed by the term.

In this embodiment, as best illustrated in FIG. 3, the spacing member 16 protects at least a portion of the valve portion 15 from contact with the wall of the body vessel 12 as the valve portion 15 moves between the first and second positions. This protection prevents the protected portion of the valve portion 15 from contacting the wall of the body vessel 12. This may be particularly advantageous if the valve portion 15 comprises an ECM or other bioremodellable material, as the spacing member 16 will prevent attachment and/or incorporation of the valve portion 15 with the wall of the body vessel 12. If a valve portion 15 comprising an ECM is allowed prolonged and/or repeated contact with the wall of the body vessel 12, the valve portion 15 may become fixed in an open or partially open configuration as the ECM becomes incorporated into the vessel wall. If incorporation occurs, performance of the valve 10 may be affected. The invention overcomes this concern because the spacing member 16 disposed on the valve portion 15 substantially prevents such contact between the valve portion 15 and the vessel wall. That is, the spacing member 16 protects the valve portion 15 from contact with the vessel wall. It is believed that the invention may also prevent or reduce formation of thrombus on or near the valve portion 15.

For all embodiments of the invention, the spacing member, no matter the size, shape, or configuration, can comprise any suitable material. Examples of suitable materials for the spacing member include natural and synthetic materials. Examples of suitable natural materials include ECMs and other bioremodellable materials that have been treated to be biologically inert, i.e., no longer capable of remodeling. An example of a suitable such material is fixed SIS. Examples of suitable synthetic materials include polymeric materials, such as polypropylenes and polyethylenes. A combination of natural and synthetic materials can also be used. The spacing member can also comprise a resorbable material. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

It is believed that a material with certain properties can provide advantages over other materials for use in the spacing member. For example, lipophobic and/or hydrophilic materials may provide effective protection to a valve portion of a valve member, by providing desirable chemical properties that may facilitate the protection from prolonged contact with a vessel wall or other structural member of the valve.

If the spacing member 16 is disposed only on the valve portion 15, another portion of the valve member 14, such as a peripheral portion, may become incorporated into the wall of the vessel 12 while the valve portion 15 does not become incorporated. This might allow implantation of a prosthetic valve in a body vessel while preventing the unintended fixing of a valve portion in an open configuration, as mentioned above. In the embodiment illustrated in FIGS. 1 through 3, the spacing member 16 is disposed on the valve portion 15, but not on other portions of the valve member 14, such as peripheral portions 25 and 27. This configuration allows peripheral portions 25, 27 to eventually become incorporated into the wall of the vessel 12, while protecting the valve portion 15 from such incorporation. In this embodiment, the spacing member 16 is disposed entirely on the valve portion 15, which is moveable between first and second positions, and is not disposed on other portions of the valve member 14, such as other non-moveable portions. While this configuration may provide benefits, it is not required in all embodiments of the invention.

With some materials, such as ECMs, the need for protection of the valve portion from repeated and/or prolonged contact with a wall of the body vessel must be balanced against the need for cellular access to the material of the valve portion to allow the remodeling effect to occur. For example, for SIS to remodel in one desired manner, access to the material by endothelial cells is important. Cellular access allows endothelial cells to associate with the SIS and colonize the material. If this access is hindered or blocked, colonization, and ultimately remodelling, may not occur completely. Thus, it may be desirable to utilize a spacing member that does not completely block cellular access to the valve portion of the valve member. Cellular access to the material can be provided in various manners, such as by employing a spacing member that comprises a porous material, and/or positioning the spacing member in a pattern and/or configuration that does not block access to the entire valve portion.

FIGS. 4 through 7 illustrate a prosthetic valve 110 according to another embodiment of the invention. In this embodiment, the prosthetic valve 110 comprises a valve member 114 that comprises a valve portion 115. The prosthetic valve 110 further comprises a second valve member 114' that comprises a second valve portion 115'. Each of the valve portions 115, 115' are movable between first and second positions. The first valve member 114 comprises a first edge 117 and the second valve member 114' comprises a second edge 119. The first 117 and second 119 edges cooperate to define a temporary opening 126. The valve members 114, 114' are attached to a support frame 124 and can be described as valve leaflets.

The support frame 124 can comprise any suitable support frame with any suitable configuration for supporting the valve members 114, 114'. A wide variety of support frames are known in the art, and any suitable support frame can be utilized. The support frame 124 can provide a stenting function, i.e., exert a radially outward force on the interior vessel wall, but this function is not necessary. By including a support frame having stenting properties, the medical devices of the invention can provide both a stenting and a valving function at a point of treatment.

The stent art provides numerous support frames acceptable for use in the invention, and any suitable stent can be used as the support frame. The support frame need only provide the desired support member for the valve member. The specific support frame chosen will depend on numerous factors, including the vessel in which the device is being implanted, the axial length of the treatment site, the number of valves desired in the support frame, the inner diameter of the vessel, the desired delivery method for placing the support frame and valve, and others. Those skilled in the art can determine an appropriate support frame based on these various factors.

The support frame can be either self-expandable or balloon expandable. A balloon expandable support frame may provide an advantage to treatment sites where stenting function has particular importance. A self-expandable support frame may provide for relatively simple deployment at a point of treatment in a body vessel.

The support frame can be made from a variety of materials, and need only be biocompatible, or able to be made biocompatible, and provide a stenting function, if desired. Examples of suitable materials include, without limitation, stainless steel, nickel titanium (NiTi) alloys, e.g., nitinol, other shape memory and/or superelastic materials, polymers, and composite materials. Stainless steel and nitinol are particularly well-suited for use in the invention due to their biocompatibility, shapeability, and well-characterized nature.

The support frame can also have a variety of configurations, including braided strands, helically wound strands, ring members, consecutively attached ring members, tube members, and frames cut from solid tubes.

Examples of suitable support frames for use in medical devices according to the present invention include those described in U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; and published application for United States patent 20010039450 to Pavcnik et al. for an IMPLANTABLE MEDICAL DEVICE, all of which are hereby incorporated by reference in their entirety.

Figure 7:
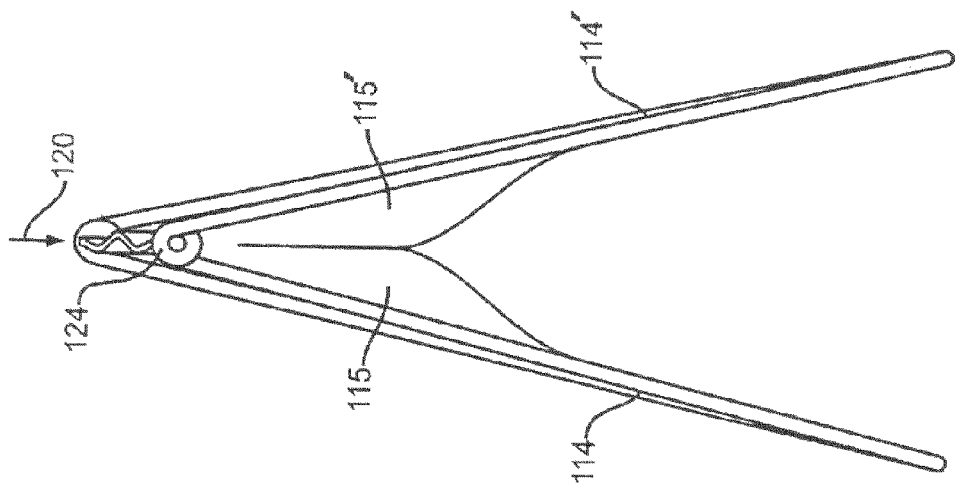
FIG. 7 is a side view of the valve illustrated in FIG. 5.
Figure 6:
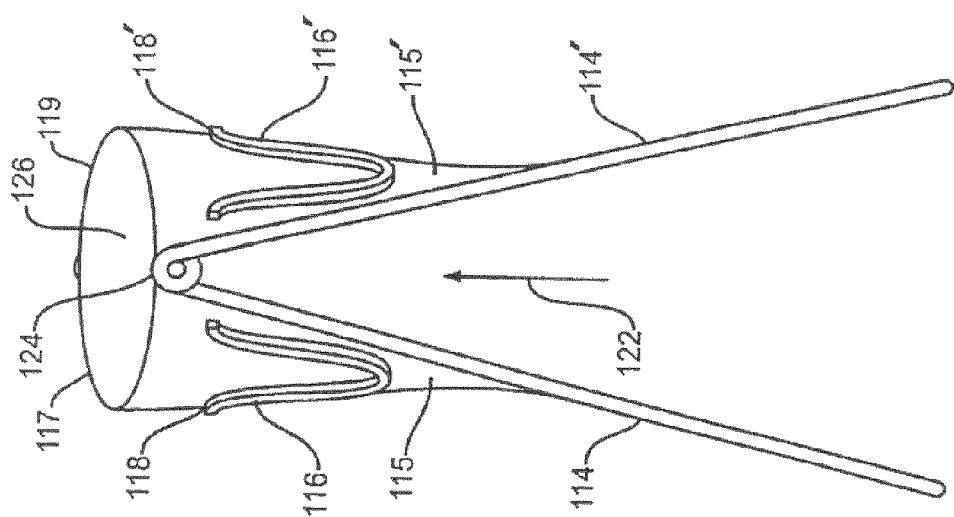
FIG. 6 is a side view of the valve illustrated in FIG. 4.

As best illustrated in FIGS. 6 and 7, the valve portions 115, 115' respond to fluid flow in one direction, represented by arrow 122, by moving into a first position in which edges 117, 119 define opening 126. In this configuration, fluid flow can pass through the valve 110. The valve portions 115, 115' respond to fluid flow in the opposite direction, represented by arrow 120, to close the opening 126 and substantially prevent fluid flow through the prosthetic valve 110 in this direction.

In this embodiment, the spacing member 116 comprises a strand of material disposed on the valve portion 115. As used herein, the term "strand" refers to a structure having a thickness, and a length that is greater than its width. In all embodiments, the spacing member 116, no matter the form, can be attached to the valve portion in any suitable manner, such as with adhesives, bonding, and by weaving through a thickness of the valve portion 115.

As illustrated in FIG. 6, a second spacing member 116' can be disposed on the second valve portion 115'. In this embodiment, the spacing members 116, 116' comprise strands that are arranged in a serpentine pattern. The spacing members 116, 116' can be arranged on the valve portions 115, 115' in any suitable configuration. Ideally, the spacing members 116, 116' are arranged on the valve portions 115, 115' such that a substantial portion of each of the valve portions 115, 115' is protected from a wall of a body vessel in which the prosthetic valve 110 may be implanted. Further, the spacing members 116, 116' can be arranged such that space exists on the valve portions 115, 115' that is not blocked by the spacing members 116, 116'. These free spaces on the valve portions 115, 115' may allow cellular access, which may facilitate any remodeling effect that may occur.

FIGS. 8 and 9 illustrate a prosthetic valve 210 according to another embodiment of the invention. In this embodiment, a spacing member 216, which is in the form of a strand, is disposed on the valve portion 215 and passes through a thickness 230 of the valve portion 215. This arrangement results in a portion 232 of the spacing member 216 on an opposing side of the valve portion 215 than other portions of the spacing member 216. This arrangement of the spacing member 216 and valve portion 215 may facilitate fabrication of the prosthetic valve 210, and may enhance a connection between the valve portion 215 and the spacing member 216. The spacing member 216 could also be partially disposed in a thickness 230 of the valve portion 215. As used herein, the term "a thickness," in relation to a valve member and valve portion, refers to any thickness of these components, including both entire and partial thicknesses.

Figure 10:
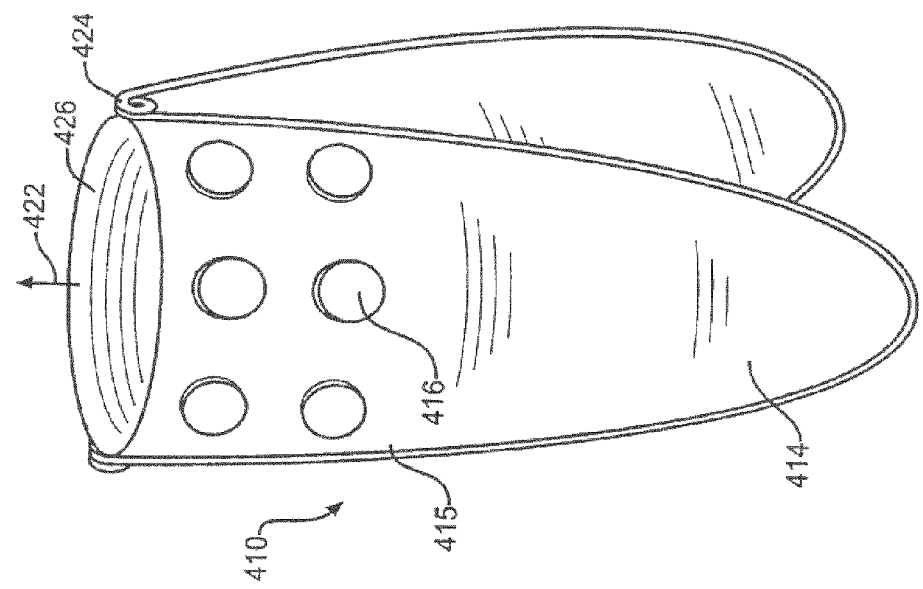
FIG. 10 is a perspective view of a prosthetic valve according to one embodiment of the invention.

FIG. 10 illustrates a prosthetic valve 310 according to another embodiment of the invention. In this embodiment, the spacing member 316 comprises a plurality of strands disposed on the valve portion 315. As illustrated in the figure, the strands can be arranged such that one strand 340 intersects another strand 342 at an intersection point 344. The use of one or more intersection points 344 provides an increased thickness at the points 344, which is expected to facilitate protection of the valve member 314. Intersection of one or more strands 340, 342 also allows for efficient organization of the strands 340, 342, which may maximize the protective effect of the spacing member 316 while still allowing cellular access to the valve member 314 for remodelling. Also in this embodiment, the spacing member 316 is disposed on the valve portion 315, as well as on other portions of the valve member 314.

Figure 11:
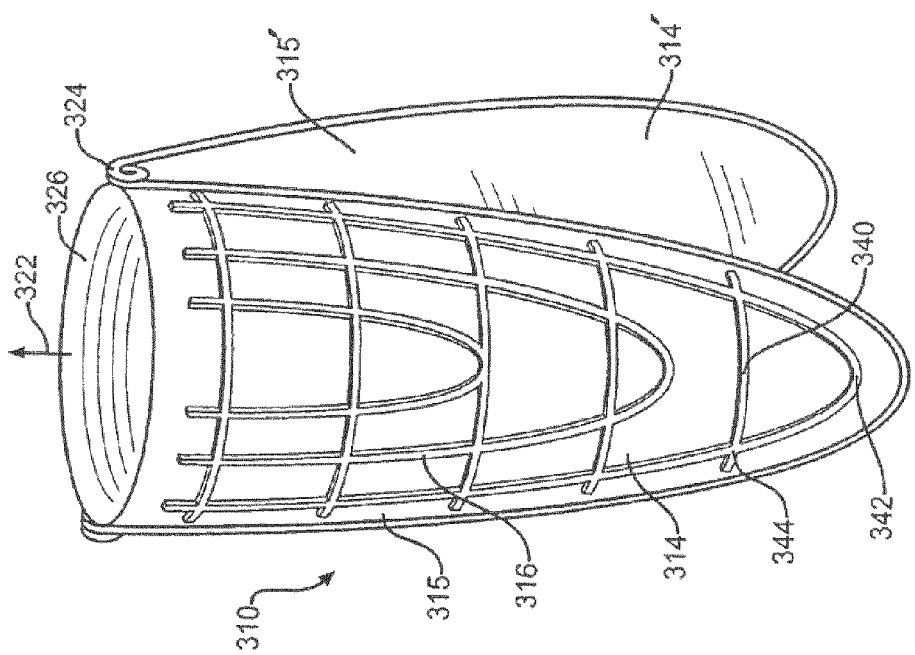
FIG. 11 is a perspective view of a prosthetic valve according to one embodiment of the invention.

FIG. 11 illustrates a prosthetic valve 410 according to another embodiment of the invention. In this embodiment, the spacing member 416 comprises a disc of material disposed on the valve portion 415 of the valve member 414. The disc, as shown in the figure, has a substantially circular shape. It is contemplated, however, that the spacing member 416 can have any suitable size, shape, and overall configuration. For example, the spacing member 416 can have a square, triangular, rectangular, or elliptical cross-sectional shape. Also, the spacing member 416 can have a conical configuration. Also, the spacing member 416 can include a portion that is disposed in a thickness of the valve portion 415. The exact size, shape, and configuration chosen for the spacing member 416 will depend on several factors, such as the extent of protection desired for the valve portion 415 and the need for cellular access to the valve portion 415.

A plurality of the spacing members 416 can be arranged in any suitable configuration on the valve portion 415. The specific arrangement chosen for a plurality of spacing members 416 should balance the desire for protection of the valve portion 415 from a wall of the body vessel in which the prosthetic valve 410 will be implanted and the need for cellular access to permit remodeling to occur, as discussed above.

Figures 12, 13:
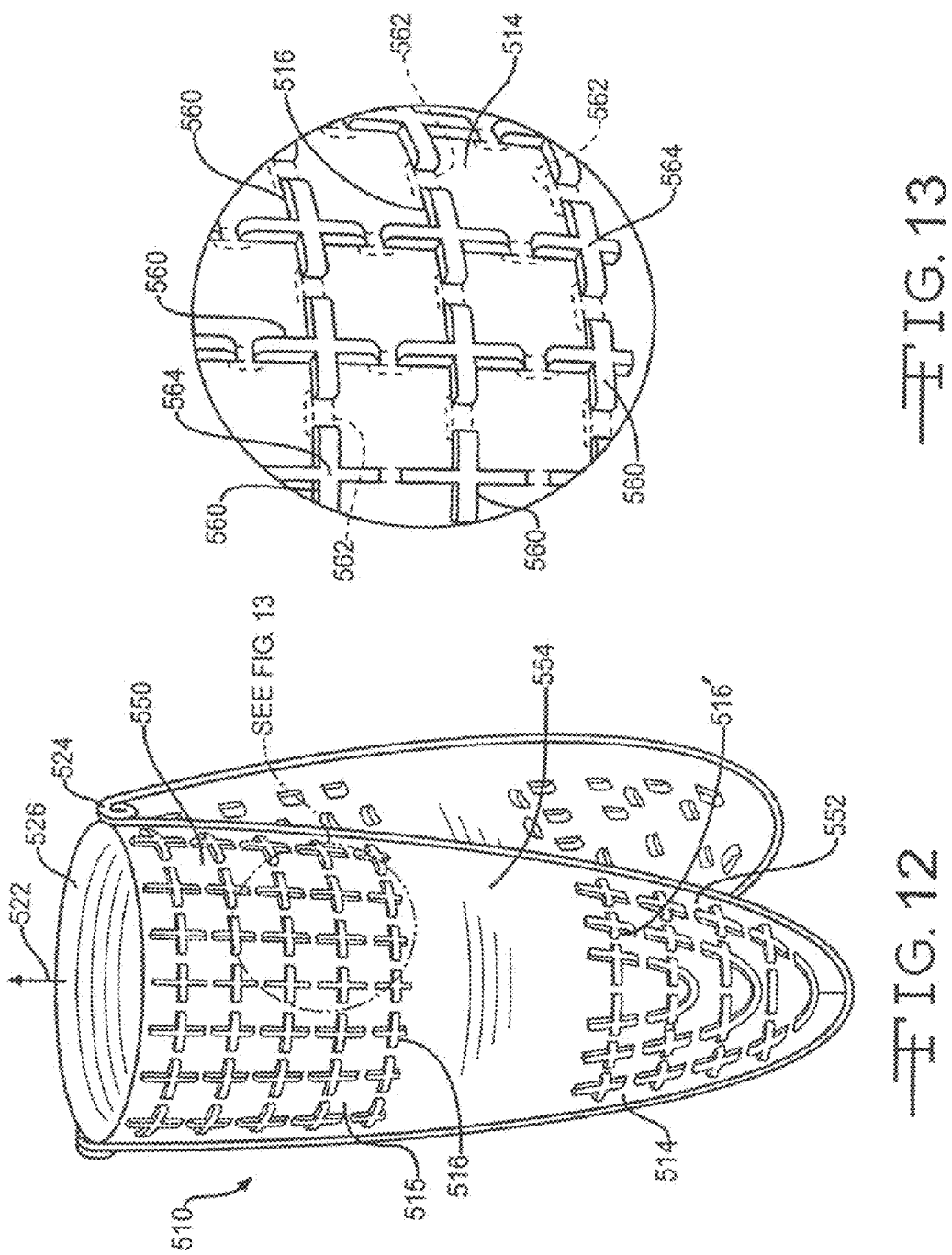
FIG. 12 is a perspective view of a prosthetic valve according to one embodiment of the invention.
FIG. 13 is a magnified view of area A highlighted in FIG. 12.

FIGS. 12 and 13 illustrate a prosthetic valve 510 according to another embodiment of the invention. In this embodiment, the valve member 514 comprises first 550 and second 552 sections. The first section 550 can include the valve portion 515 of the valve member. The sections 550, 552 are distinct sections on the valve member 514, and can abut one another, or can be separated by a third section 554, as illustrated in the figure. The spacing member 516 is disposed on the first section 550. A second spacing member 516' can be disposed on the second section 552. The third section 554 can be substantially free of the spacing members 516, 516', which may allow movement of the valve portion 515 about a point in the third section 554. This configuration is expected to allow the spacing members 516, 516' to provide protection for the first 550 and second 552 sections of the valve member 514, while allowing the desired movement of the valve portion 515 because of the substantial absence of the spacing member 516, 516' from the third section 554.

As best illustrated in FIG. 13, the spacing member 516 in this embodiment comprises a plurality of strands that are repeatedly passed through a thickness of the valve member 514. A portion of the spacing member 516 completely passes through the thickness of the valve member 514 to produce first strand portions 560 adjacent one side of the valve member 514 and second strand portions 562 adjacent an opposite side of the valve member 514. Also, the strands intersect at intersection points 564 on one or both sides of the valve member 514. As described above, the spacing member 516 can pass through a partial thickness of the valve member 514 instead of passing through an entire thickness of the valve member 514. The second spacing member 516' can also have any of these configurations, and need not have the same configuration as the first spacing member 516.

Figure 14:
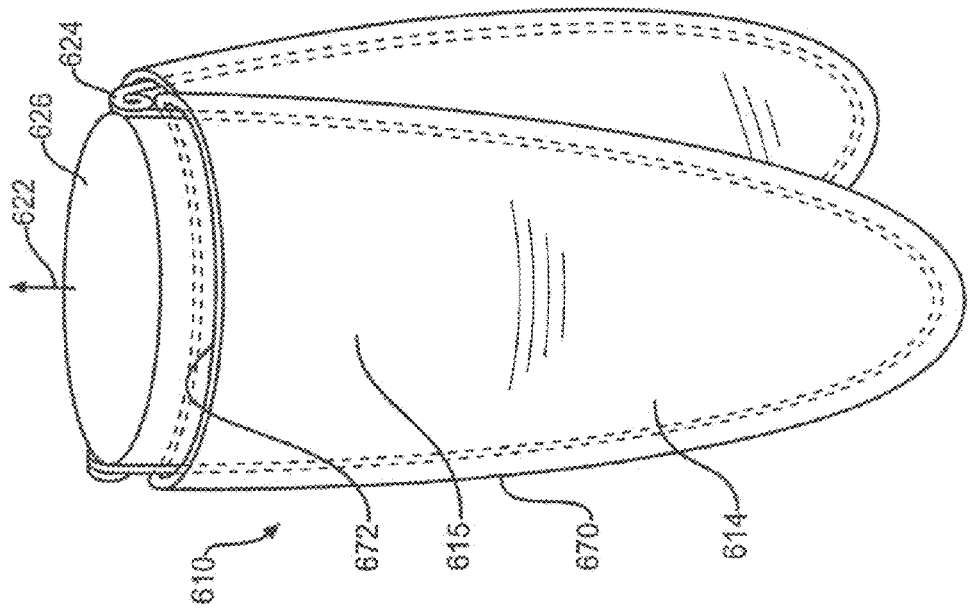
FIG. 14 is a perspective view of a prosthetic valve according to one embodiment of the invention.

FIG. 14 illustrates a prosthetic valve 610 according to another embodiment of the invention. In this embodiment, the spacing member surrounds a portion of the valve member. That is, the spacing member is disposed on first and second sides of a portion of the valve member. The spacing member can comprise a pouch 670 that defines a cavity 672. A portion of the valve member 614 is disposed in the cavity 672 of the pouch 670. This configuration of the spacing member as a pouch may facilitate fabrication of prosthetic valves according to the invention.

Figure 15:
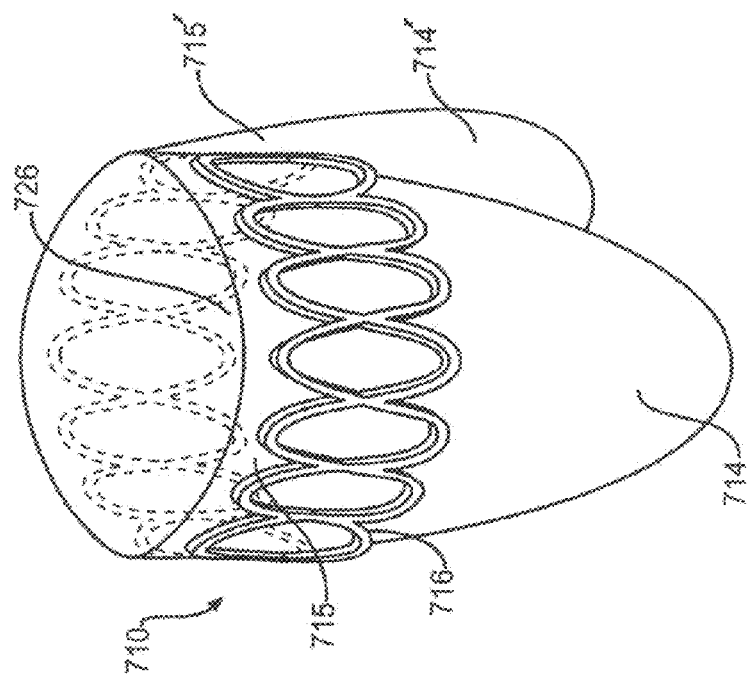
FIG. 15 is a perspective view of a valve according to one embodiment of the invention.

FIG. 15 illustrates a prosthetic valve 710 according to another embodiment of the invention. In this embodiment, the spacing member comprises an expandable support frame. The expandable support frame provides support for the valve member and also provides protection for the valve portion from contact with a wall of a vessel in which the device is implanted.

The spacing member 716 comprises an expandable support frame. The support frame has interior and exterior surfaces. The exterior surface contacts the vessel wall, while the valve member 714 is attached to the interior surface.

The support frame can be any suitable support frame as describe above, and need only provide for the desired attachment of the valve member 714 and the protection for the valve member 714 from contact with the vessel wall. The support frame can be formed of a resorbable material and can be configured to maintain the valve portion 715 in one of its two configurations until the frame is partially, substantially, or completely resorbed. This may provide a temporary protection to the valve portion 715. For example, the valve portion 715 could be held in an open configuration, as illustrated in FIG. 15, by resorbable support frame 716. The support frame 716 would protect the valve portion 715 from contacting the vessel wall. The portion of the valve member 714 on which the support frame 716 is not disposed, such as the lower portion of the valve member 714 in the figure, would not be protected and may be able to become incorporated into the vessel wall. As the support frame 716 is resorbed, the valve portion 715 would no longer be held in the open configuration and could move freely between the open and closed configurations. Ideally, remodeling of the valve portion 715 has initiated, is substantially complete, or is complete by the time at which the support frame 716 no longer provides protection from contact with the vessel wall. Also ideally, the support frame 716 provides protection to the valve portion 715 until the non-protected portion of the valve member 714 is substantially incorporated into the vessel wall. Various properties of the spacing member 716 can be manipulated to achieve these effects, including the thickness, overall amount, resorption time, composition, and other properties.

Figure 16:
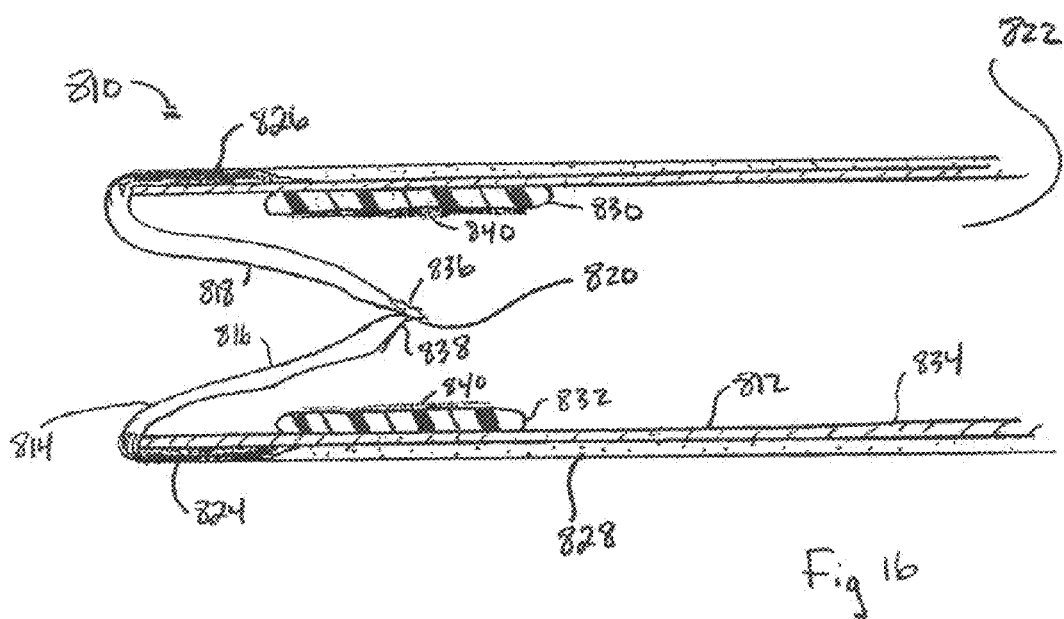
FIG. 16 is a sectional view of a prosthetic valve according to one embodiment of the invention disposed within a body vessel.

FIG. 16 illustrates a prosthetic valve 810 according to another embodiment of the invention. The valve 810 includes a support frame 812 and a graft member 814 that includes first 816 and second 818 valve portions. The valve portions 816, 818 cooperatively define a valve opening 820 that opens and closes in response to movement of the valve portions 816, 818.

In this embodiment, the support frame 812 is a tubular member and the valve portions 816, 818 are inverted into the lumen 822 of the frame 812 to form the valve opening 820. Cuff portions 824, 826 of the graft member 814 are disposed on the external surface of the support frame 812 and facilitate anchoring of the prosthetic valve 810 in a body vessel 828.

Spacing members, 830, 832 are disposed on the inner surface 834 of the support frame 812 and are positioned substantially adjacent the ends 836, 838 of the valve portions 816, 818. In this embodiment, the spacing members protect the valve portions 816, 818 from interaction with the support frame 812, particularly the ends 836, 838 of the valve portion 816, 818. This protection can be particularly important in tubular constructs due to movement of the valve portions within the lumen of the support frame.

The spacing members 830, 832 can be disposed at any suitable location on the support frame 812, including the inner and outer surfaces. In one embodiment, one or more spacing members is formed in a manner that spans one or more open cells of a support frame. In this configuration, the spacing member(s) can protect the valve portion from contacting the vessel wall through the open cells of the support frame. In this embodiment, a sleeve surrounding the support frame can be used as the spacing member. Alternatively, a member can be formed on the support frame in a manner that spans one or more open cells, such as by dipping the support frame in a polymeric material. A complete closing of one or more open cells is advantageous in these embodiments, but is not required.

The spacing members 830, 832 can be made of any suitable material, as described above. Also, the spacing members can be formed during the fabrication of the support frame 812 or can be attached to the frame 812 in subsequent steps using any suitable technique, including laser welding, soldering, radiofrequency bonding, use of adhesives and attachment members, such as clips.

As an additional layer of protection, a coating 840 can be disposed on the spacing members 830, 832 to protect the valve portions 816, 818 from adhering to the spacing members. The coating 840, if used, is advantageously disposed on a surface of the spacing members 830, 832 that may contact the valve portions 816, 818 during routine use of the prosthetic valve 810. Any suitable coating that prevents or reduces adhesion can be used, and the specific coating chosen will depend on several factors, including the material used for the valve portions 816, 818. Examples of suitable coatings include lubricious coatings, slip coatings, and other types of conventional coatings.

The spacing member can also comprise a bioactive. As used herein, the term "bioactive" refers to any composition that is believed to be capable of producing a biological and/or treatment effect in a host. The term includes compositions that directly produce biological effects, as well as compositions that produce, generate, or otherwise provide another composition that produces a biological effect. In embodiments in which the spacing member comprises a bioactive, the spacing member serves two functions. First, the spacing member provides the desired protection for the valve portion. Second, the spacing member provides a bioactive to a tissue or into a body fluid.

Any suitable bioactive can be used in the invention, and the specific bioactive chosen will depend on the desired effect. Examples of suitable bioactives include antithrombogenic agents, antiproliferative agents, and immunosuppressive agents. A wide range of other bioactives can be used, including heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; Hytrin.®. or other antihypertensive agents; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodelling inhibitor; deoxyribonucleic acid, an antisense nucleotide or another agent for molecular genetic intervention; methotrexate or another antimetabolite or antiproliferative agent; tamoxifen citrate, Taxol.®. or the derivatives thereof, or other anti-cancer chemotherapeutic agents; dexamethasone, dexamethasone sodium phosphate, dexamethasone acetate or another dexamethasone derivative, or another anti-inflammatory steroid or non-steroidal antiinflammatory agent; cyclosporin or another immunosuppressive agent; trapidal (a PDGF antagonist), angiopeptin (a growth hormone antagonist), angiogenin, a growth factor or an anti-growth factor antibody, or another growth factor antagonist; dopamine, bromocriptine mesylate, pergolide mesylate or another dopamine agonist; $^{60}$Co (5.3 year half life), $^{192}$Ir (73.8 days), $^{32}$P (14.3 days), $^{111}$In (68 hours), $^{90}$Y (64 hours), $^{99m}$Tc (6 hours) or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine betahydroxylase conjugated to saporin or other antibody targeted therapy agents; gene therapy agents; and enalapril and other prodrugs; Proscar.®., Hytrin.®. or other agents for treating benign prostatic hyperplasia (BHP) or a mixture of any of these.

In some embodiments, the bioactive is used to inhibit restenosis, such as paclitaxel, rapamycin, and other bioactives able to inhibit restenosis of a body vessel. Also, the bioactive can comprise a bioactive capable of producing another bioactive that has a desired effect, such as a nitric oxide (NO) producing and/or releasing entity. NO may have one or more desired treatment effects, including the ability to inhibit restenosis of a body vessel. Further, the spacing member can comprise two or more bioactives.

If included, the bioactive can be associated with the spacing member in any suitable manner. For example, the bioactive can be coated on a surface of the spacing member, disposed in a discrete portion of the spacing member, and dispersed throughout a portion, or the entirety, of the spacing member. The exact manner of associating the bioactive with the spacing member will depend on numerous factors, which may include the nature of the bioactive and/or spacing member, manufacturing methods, and desired treatment effect. Those skilled in the art can choose an appropriate manner of associating the bioactive with the spacing member based on these and/or other factors.

The spacing member may also comprise a barrier that controls release of the bioactive from the spacing member. For example, the spacing member can include a layer of the bioactive, either alone or with another material, and a barrier layer disposed on the bioactive layer. Also, the bioactive can be distributed in a barrier. In these embodiments, the barrier need only comprise a material that provides a controlled release of the bioactive from the spacing member. For example, the barrier can be a polymer that controls release of the bioactive by diffusion of the bioactive through the polymer or degradation of the polymer. Furthermore, blends and layering of polymer(s) can be used to create a barrier. Examples of suitable arrangements of barriers are in U.S. Pat. No. 6,299,604 to Ragheb for a COATED IMPLANTABLE MEDICAL DEVICE, which is hereby incorporated by reference in its entirety.

The invention also provides methods of making medical devices. In some embodiments, methods according to the invention comprise methods of making prosthetic valves. One method according to the invention comprises providing a valve member comprising a valve portion that is moveable between first and second positions and disposing a spacing member on the valve portion. The disposing step can be accomplished in any suitable manner, which can include adhering, such as by using adhesives, bonding, and weaving. For example, to weave the spacing member with the valve portion, the method can comprise disposing a portion of the spacing member on the valve portion and passing a portion of the spacing member through a thickness of the valve portion. The thickness can be an entire or a partial thickness. Further, the spacing member can be repeatedly passed through a thickness of the valve portion.

The spacing member used in the methods of making a medical device according to the invention can comprise any suitable spacing member. Examples of suitable spacing members include those described herein, such as strands and pouches. In one method, a pouch defining a cavity is provided, and a portion of a valve member is disposed in the cavity.

Also, the spacing member can comprise a resorbable support frame. In one embodiment, a method of making a medical device according to the invention comprises providing a resorbable support frame, providing a valve member, and attaching the valve member to the support frame so that the valve member comprises a valve portion moveable between first and second positions and so that the support frame temporarily maintains the valve member in the first position. The temporary maintenance of the valve member in the first position can endure until resorption of the support frame is initiated, is partially complete, is substantially complete, or is complete.

The invention also provides methods of treatment. Methods of treatment according to the invention include implanting any medical device according to the invention in a body vessel at a point of treatment. One method according to the invention comprises providing a prosthetic valve comprising a valve member comprising a valve portion moveable between first and second positions, and a support frame attached to the valve portion and adapted to maintain the valve portion in the first position for a period of time. Another step of the method comprises implanting the prosthetic valve in a body vessel. The implanting step can be accomplished by any suitable technique, including surgical implantation and percutaneous delivery to a point of treatment in the body vessel. The technique chosen will depend on several factors, including the configuration of the prosthetic valve.

All components, features, and characteristics of embodiments described herein are not limited to the embodiment for which they are described and/or illustrated.

The embodiments described and illustrated herein provide examples of the invention, and are not intended to limit the scope of the invention in any manner. Rather, they serve only to aid those skilled in the art to make and use the invention.

I claim:

1. A prosthetic valve for implantation in a body vessel, said prosthetic valve comprising:
    an expandable support frame comprising a resorbable material and having an interior surface and an exterior surface adapted to contact a vessel wall of said body vessel;
    a valve member comprising a lower portion and a valve portion moveable between a first position to allow fluid flow through said body vessel and a second position to substantially prevent fluid flow through said body vessel, the lower portion being free of contact with the expandable support frame and the valve portion attached to the interior surface of the expandable support frame such that the expandable support frame temporarily maintains the valve member in the first position and protects the valve portion from contacting the vessel wall.

2. The prosthetic valve according to claim 1, wherein the expandable support frame comprises a self-expandable support frame.

3. The prosthetic valve according to claim 1, wherein the expandable support frame defines a plurality of open cells.

4. The prosthetic valve according to claim 3, wherein the valve portion of the valve member spans each open cell of the plurality of open cells.

5. The prosthetic valve according to claim 1, wherein the valve member comprises a first movable leaflet having a first edge and a second movable leaflet having a second edge.

6. The prosthetic valve according to claim 5, wherein the first and second edges cooperate to define an opening adapted to open to allow fluid flow through said body vessel and close to substantially prevent fluid flow through said body vessel following resorption of the expandable support frame.

7. The prosthetic valve according to claim 1, wherein the resorbable material is selected from the group consisting of resorbable homopolymers, copolymers, and blends of resorbable polymers.

8. The prosthetic valve according to claim 1, wherein the resorbable material is selected from the group consisting of poly alpha hydroxy acids, polylactic acid, polylactide, polyglycolic acid (PGA), polyglycolide, trimethlyene carbonate, polycaprolactone, poly-beta hydroxy acids, polyhydroxybutyrate, polyhydroxyvalerate, polyphosphazines, polyorganophosphazines, polyanhydrides, polyesteramides, polyorthoesters, polyethylene oxide, polyesterethers, polyamino acids, poly-L-glutamic acid, and poly-L-lysine.

9. A prosthetic valve according to claim 1, wherein the resorbable material comprises polyglycolic acid.

10. The prosthetic valve according to claim 1, wherein the valve member comprises a bioremodellable material.

11. The prosthetic valve according to claim 10, wherein the bioremodellable material comprises an extracellular matrix material.

12. The prosthetic valve according to claim 10, wherein the bioremodellable material comprises small intestine mucosa.

13. A prosthetic valve according to claim 10, wherein the expandable support frame is configured to protect the valve portion from contacting the vessel wall until the lower portion of the valve member is substantially incorporated in the vessel wall of said body vessel.

14. A prosthetic valve for implantation in a body vessel, said prosthetic valve comprising:
- a self-expandable support frame comprising a resorbable material and having an interior surface and an exterior surface adapted to contact a vessel wall of said body vessel;
- a valve member formed of a bioremodellable material and comprising a lower portion and a valve portion moveable between a first position to allow fluid flow through said body vessel and a second position to substantially prevent fluid flow through said body vessel, the lower portion being free of contact with the expandable support frame and the valve portion attached to the interior surface of the expandable support frame such that the expandable support frame temporarily maintains the valve member in the first position and protects the valve portion from contacting the vessel wall.

15. The prosthetic valve according to claim 14, wherein the valve member comprises a first movable leaflet having a first edge and a second movable leaflet having a second edge.

16. The prosthetic valve according to claim 15, wherein the first and second edges cooperate to define an opening adapted to open to allow fluid flow through said body vessel and close to substantially prevent fluid flow through said body vessel following resorption of the expandable support frame.

17. A prosthetic valve according to claim 14, wherein the resorbable material comprises polyglycolic acid.

18. The prosthetic valve according to claim 14, wherein the bioremodellable material comprises an extracellular matrix material.

19. The prosthetic valve according to claim 14, wherein the bioremodellable material comprises small intestine mucosa.

20. A prosthetic valve for implantation in a body vessel, said prosthetic valve comprising:
- a self-expandable support frame comprising a resorbable material and having an interior surface and an exterior surface adapted to contact a vessel wall of said body vessel;
- a valve member formed of a bioremodellable material and comprising a first leaflet having a first edge and a second leaflet having a second edge, each of the first and second leaflets having a lower portion free of contact with the expandable support frame and a valve portion attached to the interior surface of the expandable support frame;
- wherein the first and second edges cooperate to define an opening adapted to open to allow fluid flow through said body vessel and close to substantially prevent fluid flow through said body vessel following resorption of the expandable support frame.

* * * * *